US010909548B1

(12) United States Patent
Kerner et al.

(10) Patent No.: US 10,909,548 B1
(45) Date of Patent: Feb. 2, 2021

(54) APPARATUS, SYSTEM AND METHOD FOR FACILITATING TRACKING OF CONSUMABLE PHARMACEUTICAL ARTICLES

(71) Applicant: Tri-Star Technologies, El Segundo, CA (US)

(72) Inventors: Alex Aron Kerner, Pacific Palisades, CA (US); Igor Murokh, Santa Monica, CA (US)

(73) Assignee: Tri-Star Technologies, El Segundo, CA (US)

( * ) Notice: Subject to any disclaimer, the term of this patent is extended or adjusted under 35 U.S.C. 154(b) by 0 days.

(21) Appl. No.: 16/976,467

(22) PCT Filed: Feb. 28, 2019

(86) PCT No.: PCT/US2019/020146
§ 371 (c)(1),
(2) Date: Aug. 27, 2020

(87) PCT Pub. No.: WO2019/169196
PCT Pub. Date: Sep. 6, 2019

Related U.S. Application Data

(60) Provisional application No. 62/714,089, filed on Aug. 3, 2018, provisional application No. 62/636,819, filed on Feb. 28, 2018.

(51) Int. Cl.
*B41F 17/36* (2006.01)
*G06Q 30/00* (2012.01)
(Continued)

(52) U.S. Cl.
CPC ........ *G06Q 30/0185* (2013.01); *A61B 5/1176* (2013.01); *A61J 1/035* (2013.01);
(Continued)

(58) Field of Classification Search
CPC ............ G06Q 30/0185; G06Q 20/202; G06Q 20/203; G06Q 20/208; G16H 40/20;
(Continued)

(56) References Cited

U.S. PATENT DOCUMENTS 2,895,409 A 7/1959 Kekem
5,700,998 A 12/1997 Palti
(Continued)

FOREIGN PATENT DOCUMENTS

CN 204914928 U 12/2015
WO 2009051794 A1 4/2009

*Primary Examiner* — Timothy R Waggoner
(74) *Attorney, Agent, or Firm* — Lance M. Pritikin

(57) ABSTRACT

Embodiments of an apparatus, system and method for facilitating the tracking of consumable pharmaceutical articles are disclosed. A marking apparatus is configured to apply unique indelible identifiers to pharmaceutical articles at the point-of-sale. The indelible identifiers on the articles are visually or electronically readable to allow each respective article to be traced with respect to its manufacturer, prescribing physician, patient to whom it was prescribed, dispensing location, expiration date, dosage, or some combination thereof. An associated system and method may involve the provision of a remote database element configured to be in network communication between the marking apparatus, manufacturer, distributor, prescriber, dispensing location, scanning tool, or some combination thereof. The indelible identifier may initially be generated by the apparatus and then obtained and recorded by the remote database element. Alternative, the indelible identifier may initially be generated and recorded by the remote database element, then provided to the marking apparatus.

27 Claims, 10 Drawing Sheets

(51) Int. Cl.
  *G16H 40/20* (2018.01)
  *G16H 20/10* (2018.01)
  *G16H 10/60* (2018.01)
  *G06Q 20/20* (2012.01)
  *G06Q 50/26* (2012.01)
  *B65G 49/00* (2006.01)
  *A61J 7/00* (2006.01)
  *A61J 1/03* (2006.01)
  *A61B 5/1171* (2016.01)
  *G06K 9/00* (2006.01)
  *A61J 3/00* (2006.01)
  *G06K 19/06* (2006.01)

(52) U.S. Cl.
  CPC ............ *A61J 7/0069* (2013.01); *B41F 17/36* (2013.01); *B65G 49/00* (2013.01); *G06K 9/00255* (2013.01); *G06Q 20/202* (2013.01); *G06Q 20/203* (2013.01); *G06Q 20/208* (2013.01); *G06Q 50/265* (2013.01); *G16H 10/60* (2018.01); *G16H 20/10* (2018.01); *G16H 40/20* (2018.01); *A61J 3/007* (2013.01); *A61J 2200/30* (2013.01); *A61J 2205/60* (2013.01); *B65G 2201/027* (2013.01); *G06K 19/06028* (2013.01)

(58) Field of Classification Search
  CPC ...... G16H 10/60; G16H 20/10; A61B 5/1176; A61J 7/0069; A61J 2200/30; A61J 2200/60; A61J 3/007; B41F 17/36
  See application file for complete search history.

(56) References Cited

U.S. PATENT DOCUMENTS

| | | | |
|---|---|---|---|
| 5,845,264 A | 12/1998 | Nellhaus | |
| 5,992,742 A | 11/1999 | Sullivan et al. | |
| 6,429,889 B1 | 8/2002 | Murokh | |
| 6,776,340 B2 | 8/2004 | Murokh et al. | |
| 6,776,341 B1 | 8/2004 | Sullivan et al. | |
| 6,836,284 B2 | 12/2004 | Murokh et al. | |
| 6,851,615 B2 | 2/2005 | Jones | |
| 6,952,681 B2 | 10/2005 | McQuade et al. | |
| 7,059,526 B1 | 6/2006 | Sullivan et al. | |
| 7,218,395 B2 | 5/2007 | Kaye et al. | |
| 7,370,795 B2 | 5/2008 | Radatti et al. | |
| 7,370,797 B2 | 5/2008 | Sullivan et al. | |
| 7,765,106 B2 | 7/2010 | Reardan et al. | |
| 7,793,836 B2 | 9/2010 | Radatti et al. | |
| 8,286,222 B2 | 10/2012 | Silverbrook et al. | |
| 8,312,281 B2 | 11/2012 | Silverbrook et al. | |
| 8,323,623 B2 | 12/2012 | Klocke et al. | |
| 8,626,672 B2 | 1/2014 | Stuck et al. | |
| 8,712,163 B1 | 4/2014 | Osheroff | |
| 8,715,725 B2 | 5/2014 | Stuck et al. | |
| 8,719,043 B2 | 5/2014 | Polli et al. | |
| 8,734,678 B2 | 5/2014 | Marguerettaz et al. | |
| 8,738,177 B2 | 5/2014 | van Ooyen et al. | |
| 8,786,650 B1 | 7/2014 | Eller et al. | |
| 8,799,020 B2 | 8/2014 | Roberts et al. | |
| 9,189,728 B2 | 11/2015 | Stuck et al. | |
| 9,221,271 B2 | 12/2015 | Eller et al. | |
| 9,400,909 B2 | 7/2016 | Hanina | |
| 9,517,855 B2 | 12/2016 | Murokh | |
| 9,636,273 B1 | 5/2017 | Harris | |
| 9,636,927 B2 | 5/2017 | Eller et al. | |
| 10,413,484 B2 * | 9/2019 | Ito | A61J 3/007 |
| 2003/0189030 A1 | 10/2003 | Faour | |
| 2003/0233256 A1 | 12/2003 | Cardenas et al. | |
| 2006/0012821 A1 | 1/2006 | Franklin et al. | |
| 2006/0015536 A1 | 1/2006 | Buchanan et al. | |
| 2006/0062734 A1 | 3/2006 | Melker et al. | |
| 2007/0172429 A1 | 7/2007 | Gao et al. | |
| 2007/0262147 A1 | 11/2007 | Braun et al. | |
| 2009/0201324 A1 * | 8/2009 | Ashizaki | B41J 3/4071 347/7 |
| 2011/0008527 A1 | 1/2011 | Teggatz et al. | |
| 2011/0290694 A1 | 12/2011 | Fuisz et al. | |
| 2013/0244002 A1 | 9/2013 | Sanofi | |
| 2014/0168309 A1 * | 6/2014 | Morita | B41J 3/407 347/16 |
| 2015/0174916 A1 | 6/2015 | Hara et al. | |
| 2019/0290545 A1 * | 9/2019 | Imai | A61J 7/04 |

* cited by examiner

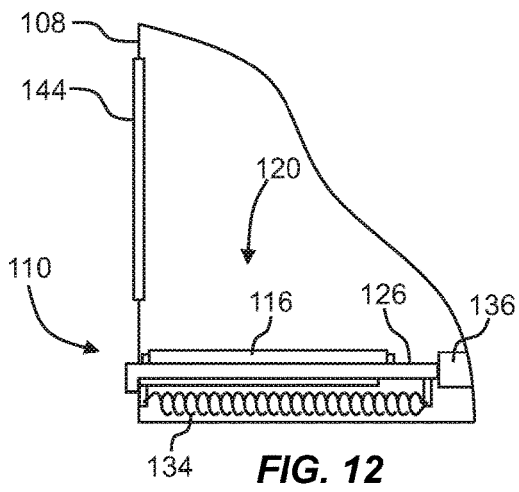
FIG. 12
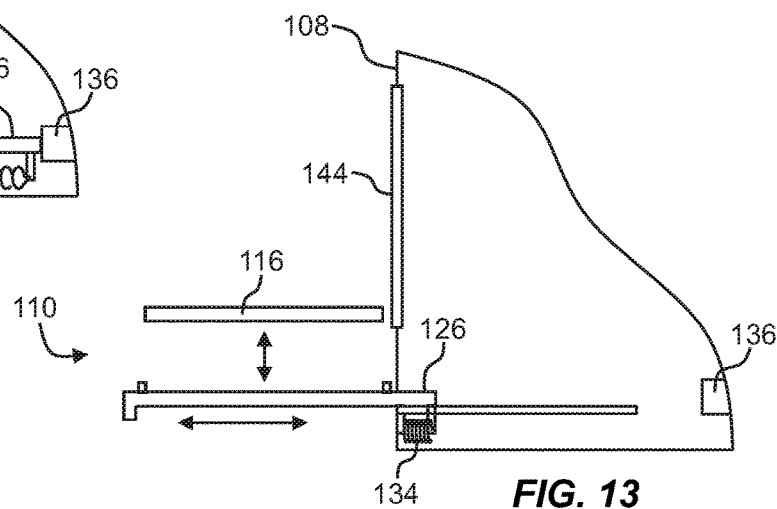
FIG. 13
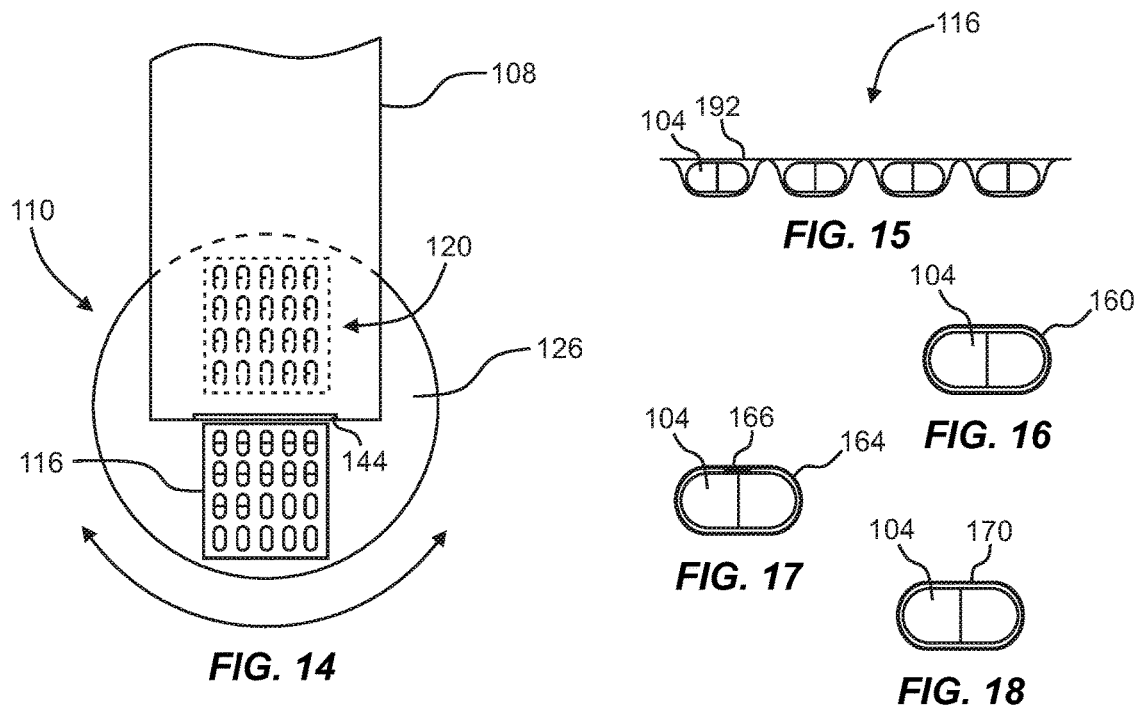
FIG. 14
FIG. 15
FIG. 16
FIG. 17
FIG. 18

APPARATUS, SYSTEM AND METHOD FOR FACILITATING TRACKING OF CONSUMABLE PHARMACEUTICAL ARTICLES

RELATED APPLICATIONS

This application is a U.S. national stage of PCT International Patent Application No. PCT/US2019/020146 having an international filing date of Feb. 28, 2019, which claims the benefit of U.S. Provisional Application No. 62/636,819 filed Feb. 28, 2018, and U.S. Provisional Application No. 62/714,089 filed Aug. 3, 2018. All of the above-identified applications are incorporated by this reference in their entireties for all purposes as if fully set forth herein.

TECHNICAL FIELD

The present disclosure relates to facilitating the tracking of the chain of custody of individual consumable articles. More particularly, the present disclosure relates to an apparatus, system and method for applying unique identifiers to individual pharmaceutical articles at a point of sale.

BACKGROUND

The opioid overdose crisis has reached epidemic levels. Nearly half of all opioid deaths involved prescription opioids. More people currently die from overdoses than they do from guns and cars. What is needed are new, more effective, cost-effective solutions for fighting the growing opioid crisis.

SUMMARY

Certain deficiencies of the prior art are overcome by the provision of embodiments of a new apparatus, system and method for implementation partially or entirely within a pharmaceutical point-of-sale location. Such apparatus, system and method involve application of indelible identifiers onto, for example, tablets and capsules at the point of sale or dispensation (e.g., pharmacies and clinics). Examples of indelible identifiers may include, for example, text, bar codes, an image of the patient's face, an RFID tag, a combination thereof or the like. This technology allows unique identifiers to be applied on each pharmaceutical article (e.g., pill, tablet or capsule) at the time it is dispensed, without damaging the originally-manufactured article, thereby providing for prescription and patient traceability, and a tool to help curb drug counterfeiting and drug overdose. Preferably, imprinting a unique identification (e.g., patient name, prescription number, etc.) on each opioid dosage, could allow local and federal law enforcement, through the use of a database, to identify and trace each prescription back to the original patient and their prescribing doctor.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 12 is a diagrammatic partial cross-sectional side view of one non-limiting example of an apparatus in accordance with the present disclosure, wherein the transport subsystem includes a shuttle element slidable with respect to the enclosure and configured to releasably support the tray element, and the transport subsystem includes a spring element for resiliently biasing the shuttle element toward placing the tray element in the loading position;

FIG. 13 is a diagrammatic partial cross-sectional view similar to that of FIG. 12, but wherein the shuttle element is shown in an extended position so as to place the tray element in the loading position, and the removability of the tray element from the shuttle element is illustrated;

FIG. 14 is a diagrammatic partial cross-sectional top view of one non-limiting example of an apparatus in accordance with the present disclosure; wherein the shuttle element is rotatable with respect to the enclosure in turntable fashion to move the tray element between the loading position and the application zone;

FIG. 15 is a diagrammatic side view of one non-limiting example of a tray element in accordance with the present disclosure, wherein the tray element is a pre-packaged blister pack housing a plurality of consumable articles in hermetically-sealed configuration, at least one side of the blister pack having a translucent or transparent layer through which the indelible identifier application is achievable without compromising the hermetic seal;

FIG. 16 is a diagrammatic cross-sectional view of one non-limiting example of a consumable article in accordance with the present disclosure, comprising a layer of digestible material deposited onto a precursor OEM-manufactured pharmaceutical article by way of an apparatus in accordance with the present disclosure;

FIG. 17 is a diagrammatic cross-sectional view of another non-limiting example of a consumable article in accordance with the present disclosure, wherein the article is a precursor OEM-manufactured pharmaceutical article encapsulated with a respective sensor sleeve by way of a presently-disclosed apparatus, the sensor sleeve having a sensor imbedded therein;

FIG. 18 is a diagrammatic cross-sectional view of a further non-limiting example of a consumable article in accordance with the present disclosure, wherein the article is a precursor OEM-manufactured pharmaceutical article with one or more layers of a marking substrate composition deposited onto the article by way of a presently-disclosed apparatus;

DETAILED DESCRIPTION OF THE PREFERRED EMBODIMENTS

Figure 1:
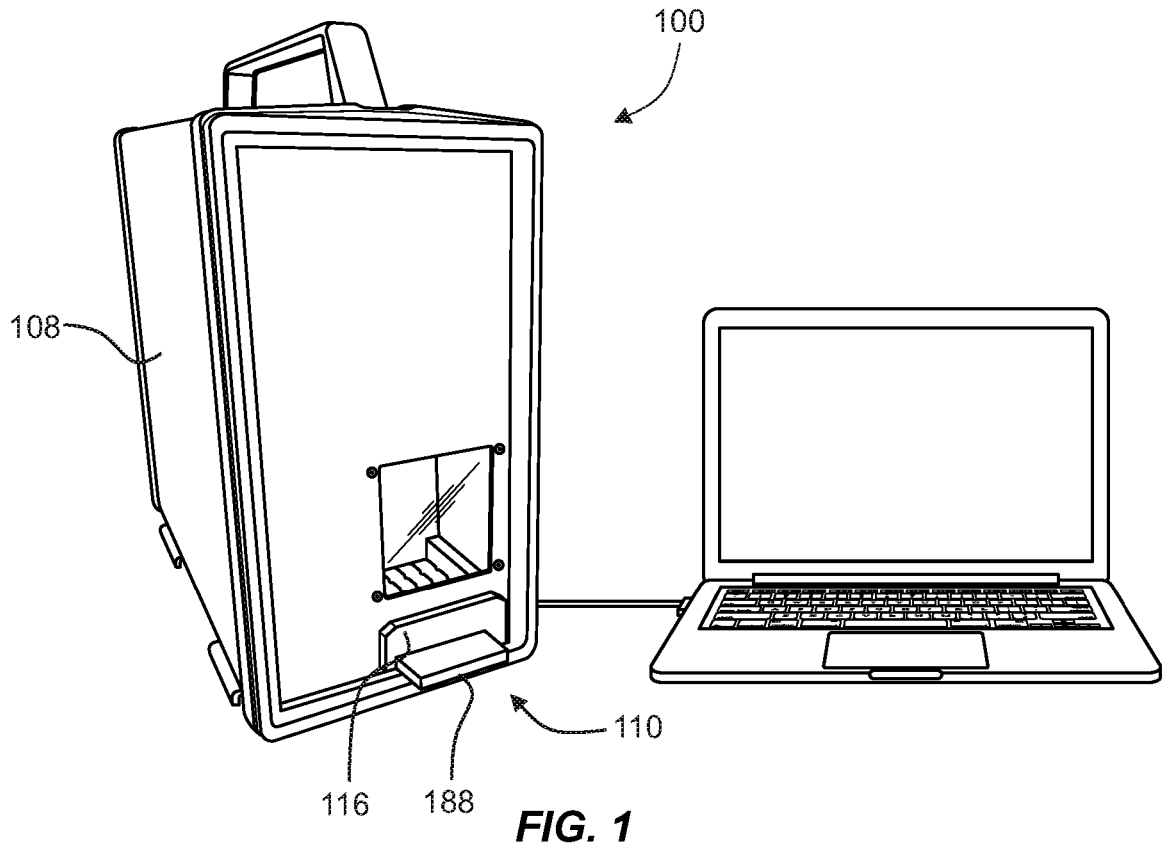
FIG. 1 is a diagrammatic perspective view of one non-limiting example of a portable point-of-sale marking apparatus in accordance with the present disclosure, wherein all or portions of the control electronics and network communication element are disposed externally of the enclosure.

Referring now to the drawings, like reference numerals designate identical or corresponding features throughout the several views.

With reference to the several drawings, a portable point-of-sale marking apparatus 100 for applying indelible identifiers 106 onto discreet consumable pharmaceutical articles 104 may comprise an enclosure 108, a transport subsystem 110, an identifier application subsystem 112 and an inspection element 114.

Figure 6:
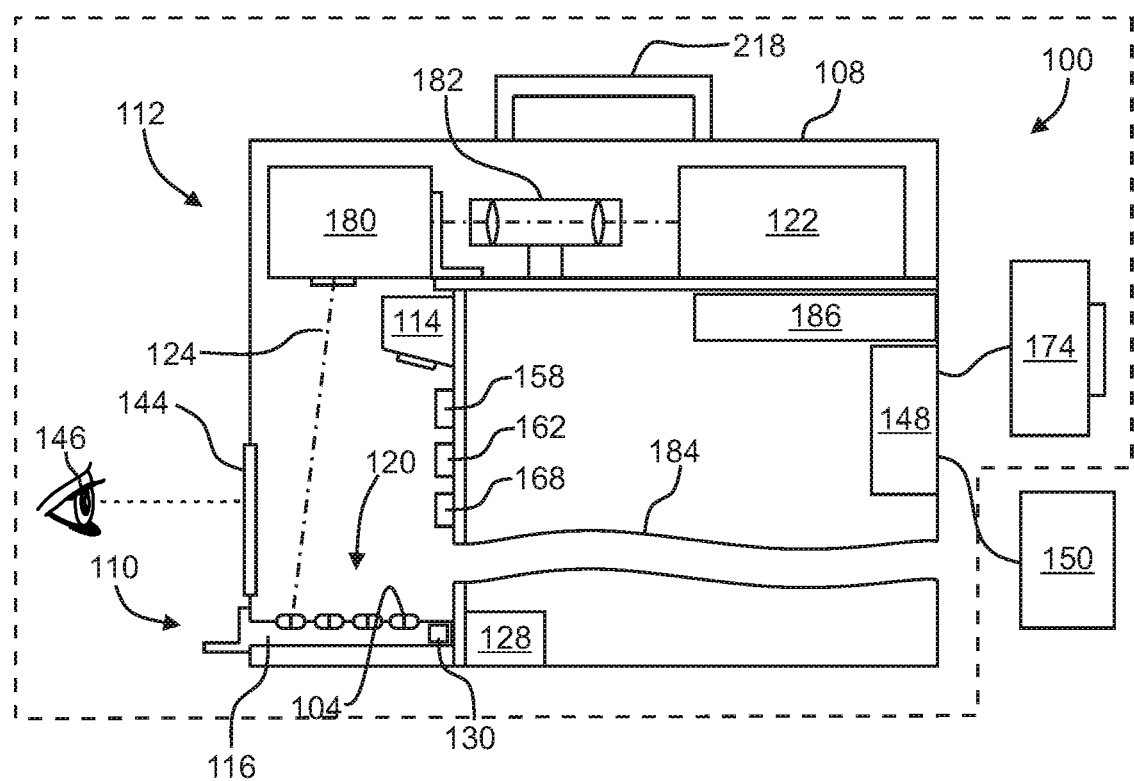
FIG. 6 is a diagrammatic cross-sectional side view of another non-limiting example of a portable point-of-sale marking apparatus in accordance with the present disclosure, wherein the control electronics and network communication element are disposed internally of a unitary enclosure, and the apparatus is shown in electrical communication with a patient camera and a remote database.
Figure 8:
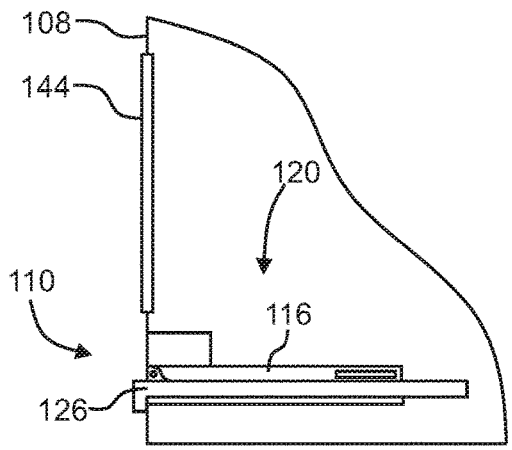
FIG. 8 is a diagrammatic partial cross-sectional side view of one non-limiting example of an apparatus in accordance with the present disclosure, wherein the tray element includes a funnel portion and is upwardly-rotatable with respect to a shuttle element.

The transport subsystem 110 may have a tray element 116 transportable between a loading position (see, for example, FIG. 9) and an application position (see, for example, FIG. 8). Referring to FIGS. 3, 4, 8 and 9 the tray element 116 may have a multiplicity of pockets 118 each configured to receive a respective said article 104, wherein (a) when the tray element 116 is in the application position (see, for example FIG. 6), its pockets 118 are located within an application zone 120 internal to the enclosure 108, and (b) when the tray element 116 is in the loading position (see, for example, FIG. 4), its pockets 118 are located externally to the enclosure 108. With reference to FIG. 6, the identifier application subsystem 112 may be positioned within the enclosure 108 for applying an indelible identifier 106 onto each said article 104 within the application zone 120. The inspection element 114 may be positioned within the enclosure 108 and may be configured to verify the quality of the indelible identifier 106 applied onto each respective article 104. The inspection element 114 may be, or may include, an inspection camera.

Figure 19:
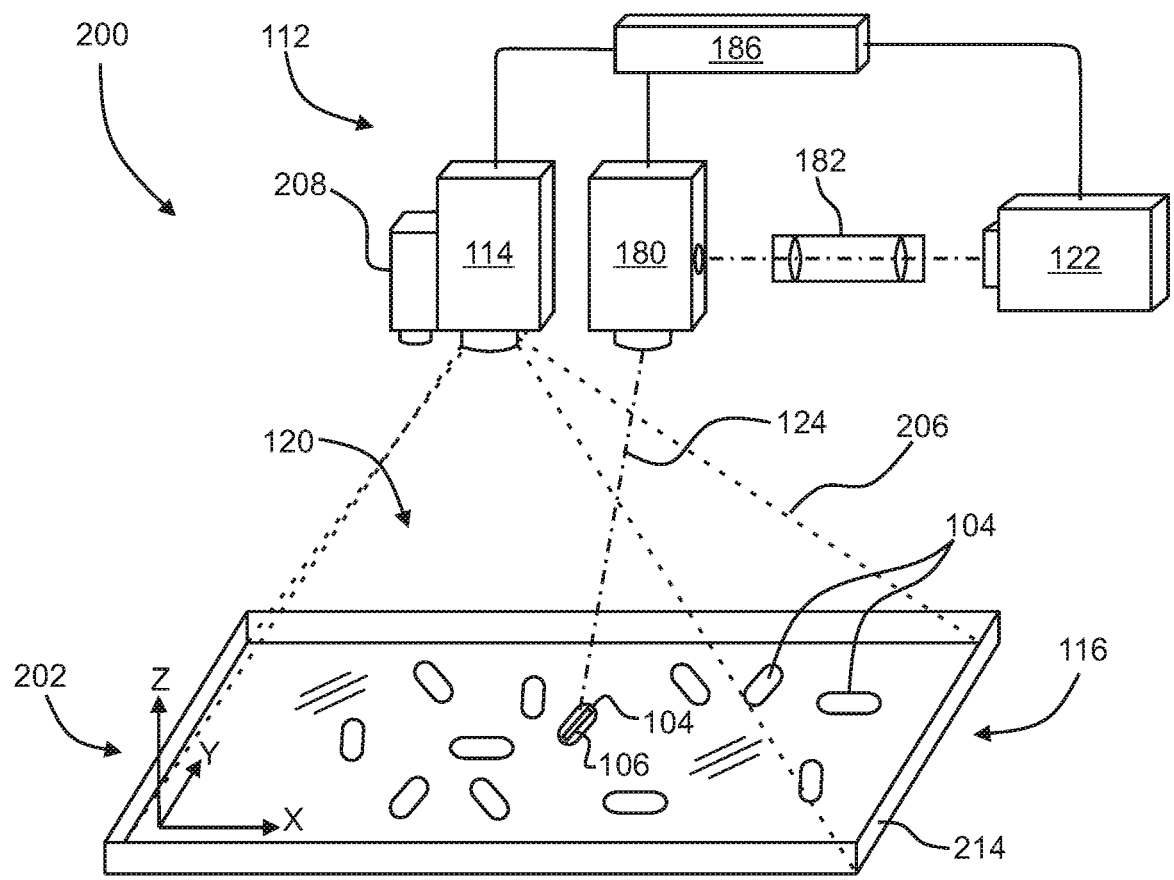
FIG. 19 is a diagrammatic perspective view of one non-limiting example of a randomized article marking system in accordance with the present disclosure.

Referring to FIGS. 6 and 19, in certain preferred embodiments of the apparatus 100 and system 200, the identifier application subsystem 112 may include a transmission element 122 (e.g., a laser transmission element) configured to direct a steered beam 124 (e.g., of UV laser energy) toward the application zone 120 for marking an indelible image 106 onto each said article 104 within the application zone 120. The identifier application subsystem 112 may further include a beam optics element 182 optically disposed between the laser transmission element 122 and a beam scanning element 180. Control electronics 186 may be programmed to control and receive data from some or all of the electronic components of the apparatus 100, such as the laser transmission element 122, beam scanning element 180 and inspection element 114. A debris vacuum hose 184 may be in debris-evacuating communication between the application zone 120 and the ambient environment external to the enclosure 108.

Referring to FIG. 6 for example illustration, in particular embodiments of the apparatus 100, the enclosure 108 may be unitary, meaning it may define a single cavity within which all of the components of the apparatus 100 are housed. The cavity may or may not be partitioned, for example, to provide internal mounting structures or airflow channels. Moreover, the enclosure may include a lift handle portion 218 to facilitate movement of the apparatus 100 within the point-of-sale location 102 by, for example, one person.

Figure 5:
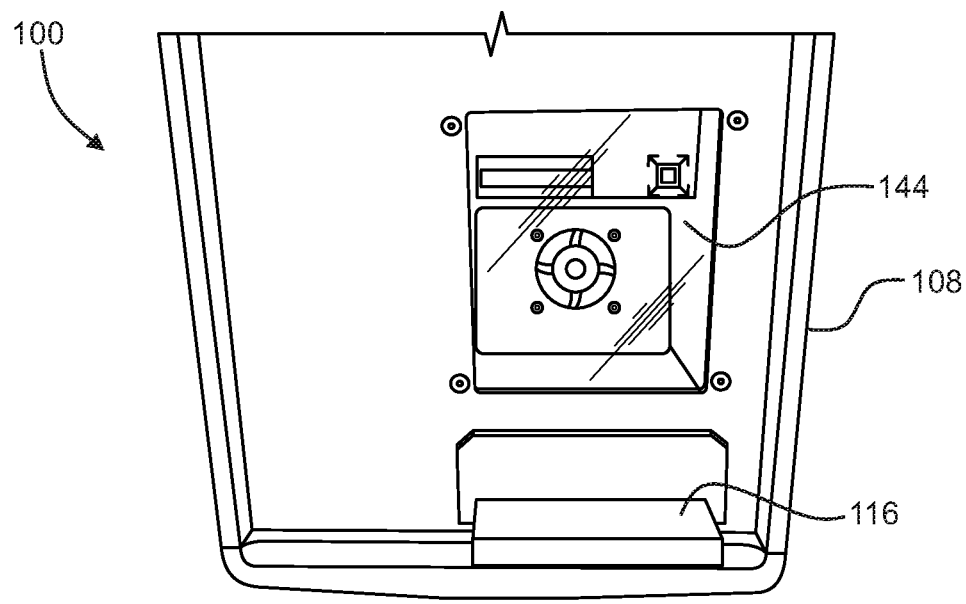
FIG. 5 is a diagrammatic partial front view of the apparatus of FIG. 1, wherein the tray element is shown in an application position.

Referring to FIGS. 1, 5 and 6 for example illustration, in certain embodiments of the apparatus 100, the transport subsystem 110 may include a handle portion 188 by which the tray element 116 is manually transportable between the loading position and the application position.

Referring to FIGS. 8-10 and 12-14 for example illustration, in particular embodiments of the apparatus 100, the transport subsystem 110 may include a shuttle element 126 slidable with respect to the enclosure 108 and configured to releasably support the tray element 116.

Referring to FIG. 6 for example illustration, the apparatus 100 may include a tray identification reader 128, and the tray element may include a tray identification element 130 readable by the tray identification reader 128. In this or other embodiments of the apparatus 100 or system 200, the apparatus or system may include a plurality of tray elements 116. In such case, the pockets 118 of each of said plurality of tray elements 116 may have a different size (e.g., width, length, diameter or a combination thereof) compared to the pockets 118 of the other tray elements 116 in the same plurality.

Figure 9:
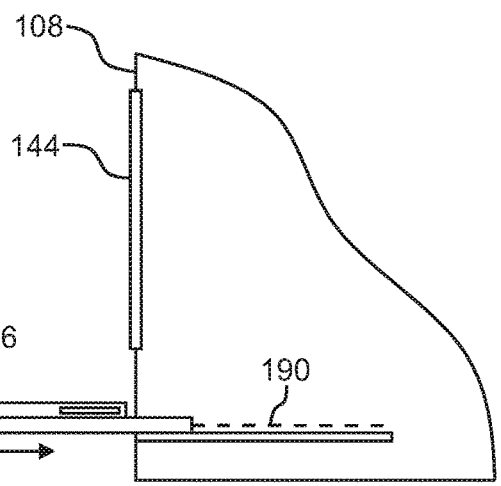
FIG. 9 is a diagrammatic partial cross-sectional side view similar to that of FIG. 8, but wherein the tray element is shown transported to the loading position by way of the shuttle element.
Figure 10:
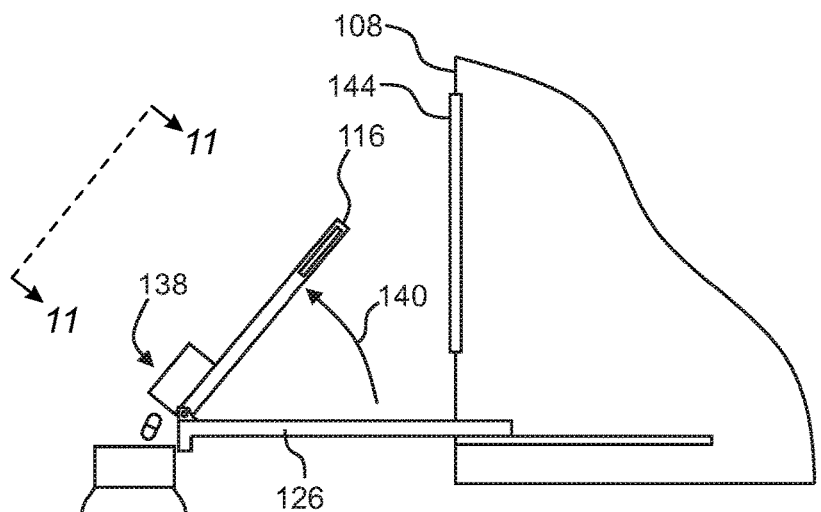
FIG. 10 is a diagrammatic partial cross-sectional side view similar to that of FIG. 9, but wherein the tray element is shown in an upwardly-rotated position thereby enabling consumable articles to be transported from respective pockets to a funnel portion by way of gravity.
Figure 11:
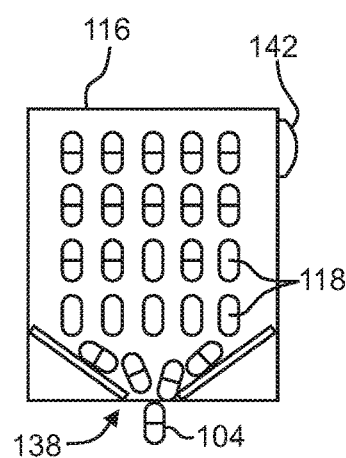
FIG. 11 is a diagrammatic plan view taken along direction 11 of FIG. 10.

Referring to FIGS. 8 and 9, the shuttle element 116 may be axially slidable with respect to the enclosure 108. Such axial slidability may be along a slide axis 190. Referring to FIGS. 12 and 13 for example illustration, the transport subsystem 110 may include a spring element 134 for resiliently biasing the shuttle element 126 toward placing the tray element 116 in the loading position. The transport subsystem 110 may include a latch element 136 for releasably retaining the tray element 116 in the application position. Alternatively, or in addition, as illustrated in FIG. 14 for example, the shuttle element 126 may be rotatable with respect to the enclosure 108 in turntable fashion so as to transport one or more tray elements 116 into and out of the application zone 120.

Referring to FIGS. 8-11 for example illustration, in certain preferred embodiments of the portable, point-of-sale marking apparatus 100, (a) the tray element 116 includes a funnel portion 138; (b) the tray element 116 is upwardly-rotatable with respect to the shuttle element 126 when releasably supported thereby; and (c) the upward rotation 140 is configured to enable consumable articles 104 to be transported from respective said pockets 118 to the funnel portion 138 by way of gravity. In such an apparatus embodiment, the tray element 116 may include a rotation handle element 142 to manually facilitate the upward rotation.

Referring to FIG. 6 for example illustration, in certain preferred embodiments of the apparatus 100, the enclosure 108 may include an application zone window portion 144 disposed between the application zone 120 and the loading position. The application zone window portion 144 may be configured to enable a naked eye of a human to view the occurrence of the application (e.g., involving transmission of laser energy) from a viewpoint 146 outward of the enclosure 108 without causing damage to the eye.

Figure 7:
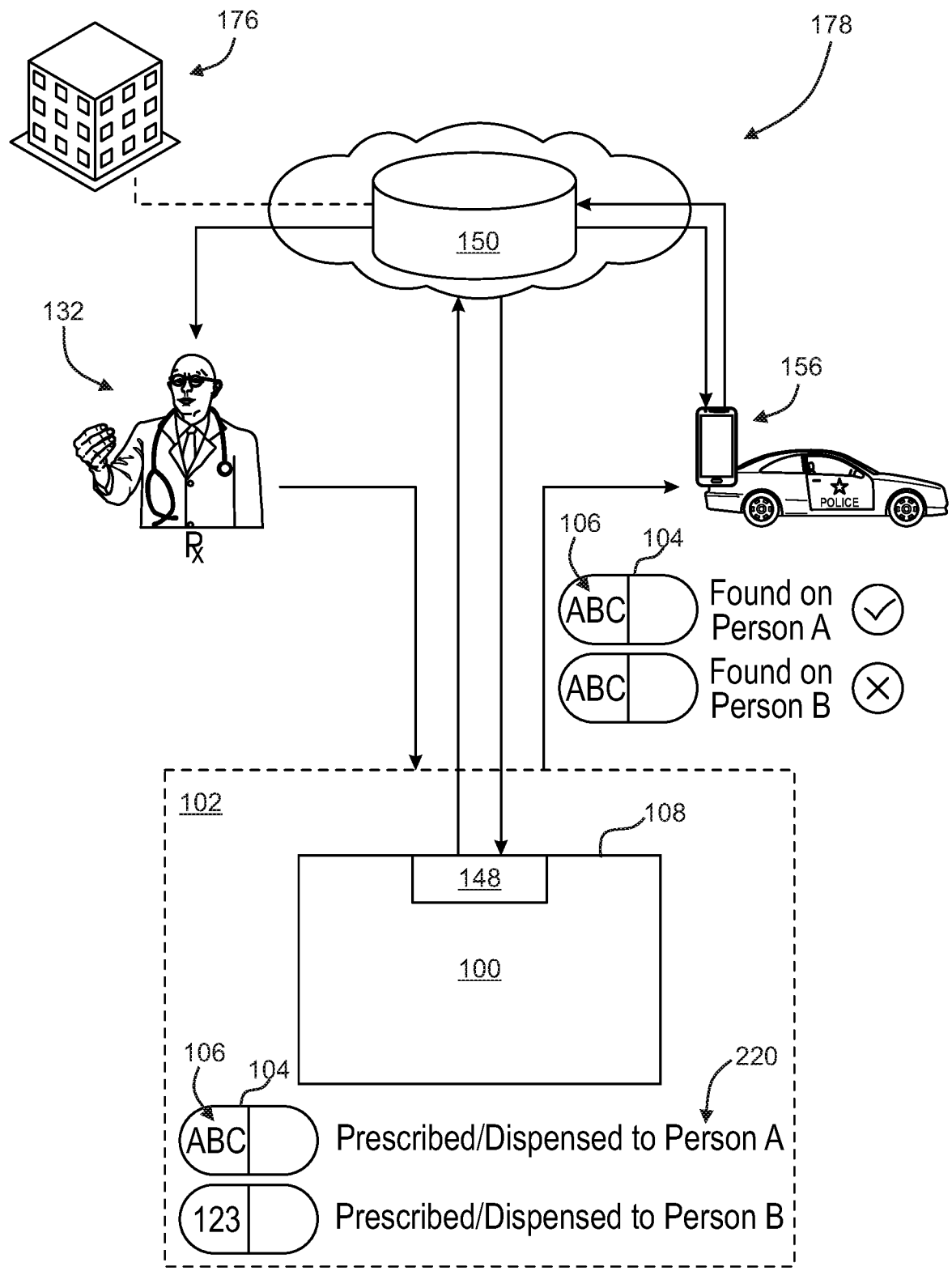
FIG. 7 is a schematic view of one non-limiting example of a system and method for facilitating tracking of consumable pharmaceutical articles in accordance with the present disclosure.

Referring to FIGS. 6 and 7 for example illustration, particular preferred embodiments of the apparatus 100 may further comprise a network communication element 148 configured to be placed in network communication with a remote database element 150. The remote database element 150 may be configured to be in data-receiving communications with a pharmaceutical manufacturer 176 or distributor 176, thereby collectively forming an embodiment of a tracking system 178 in accordance with the present disclosure. Alternatively, or in addition, the remote database element 150 may be placed (or configured to be placed) in network communication with a law enforcement scanning tool 156, thereby collectively forming an alternate embodiment of a system 178 in accordance with the present disclosure. Such scanning tool 156 may be configured to read the indelible identifier 106 and indicate whether the indelible identifier corresponds to the patient to whom the respective article was legitimately prescribed and sold.

The indelible identifier 106 may include article identifier data unique to the article 104 upon which it is applied. The article identifier data may include patient data for identifying a patient 220 to whom the respective article was prescribed and sold. Alternatively, or in addition, the article identifier data may include prescriber data for identifying a prescriber 132 by whom the respective article was prescribed. Alternatively, or in addition, the article identifier data may include prescription data for identifying the prescription number under which the respective article was sold.

Referring to FIGS. 6 and 16, certain embodiments of the apparatus 100 may further comprise a layer-depositing element 158 for depositing one or more layers 160 of digestible material into the articles 104. The one or more layers 160 may be configured to indicate whether and when the articles 104 have been consumed by a patient.

Referring to FIGS. 6 and 17, the identifier application subsystem 112 may include a sleeve-encapsulation element 162 for encapsulating each of the articles 104 with a respective sensor sleeve 164, the sensor sleeves 164 each having a sensor 166 imbedded therein.

Referring to FIG. 6, the identifier application subsystem 112 may include a marking layer applicator 168 by which the indelible identifier 106 is applied onto each said article within the application zone. Referring to FIG. 18, the marking layer applicator 168 may be configured to deposit one or more layers of a marking substrate composition 170 onto each said article 104 within the marking zone 120. The marking substrate composition 170 may comprise, for example, Titanium Dioxide or the like. The deposition may be by way of, for example, a spraying operation. Referring to FIG. 6, the identifier application subsystem 112 may include a laser transmission element 122 configured to direct a steered beam 124 of UV laser energy toward the application zone 120 for marking an indelible image 106 onto the marking substrate composition 170 deposited onto each said article within the application zone 120.

Figure 2:
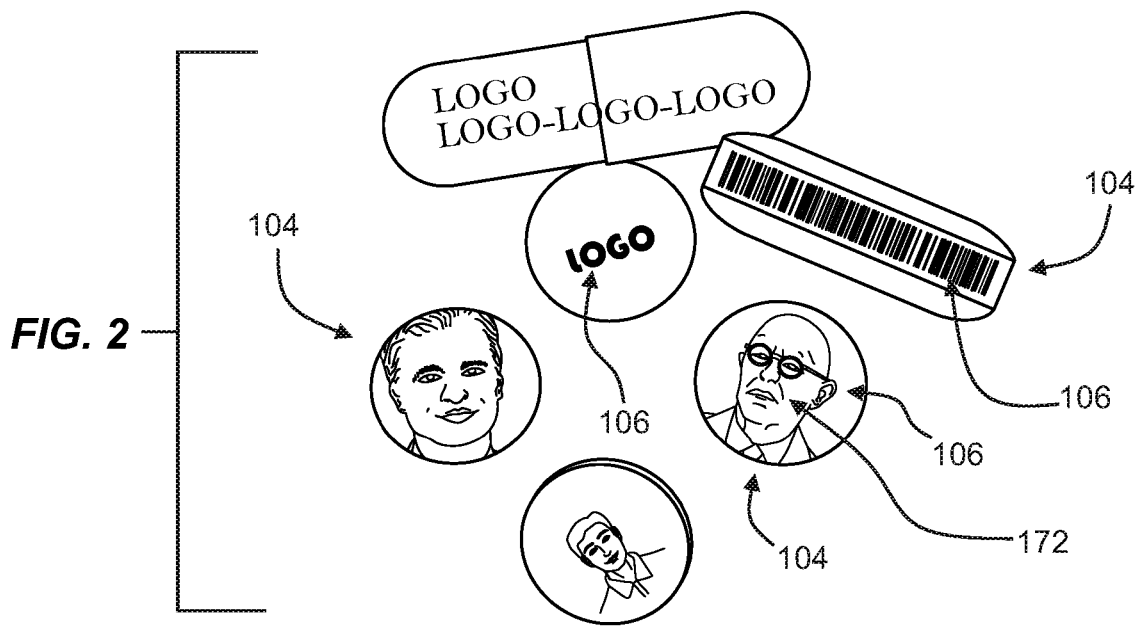
FIG. 2 illustrates various non-limiting examples of discreet consumable pharmaceutical articles with indelible identifiers in accordance with the present disclosure.
Figure 3:
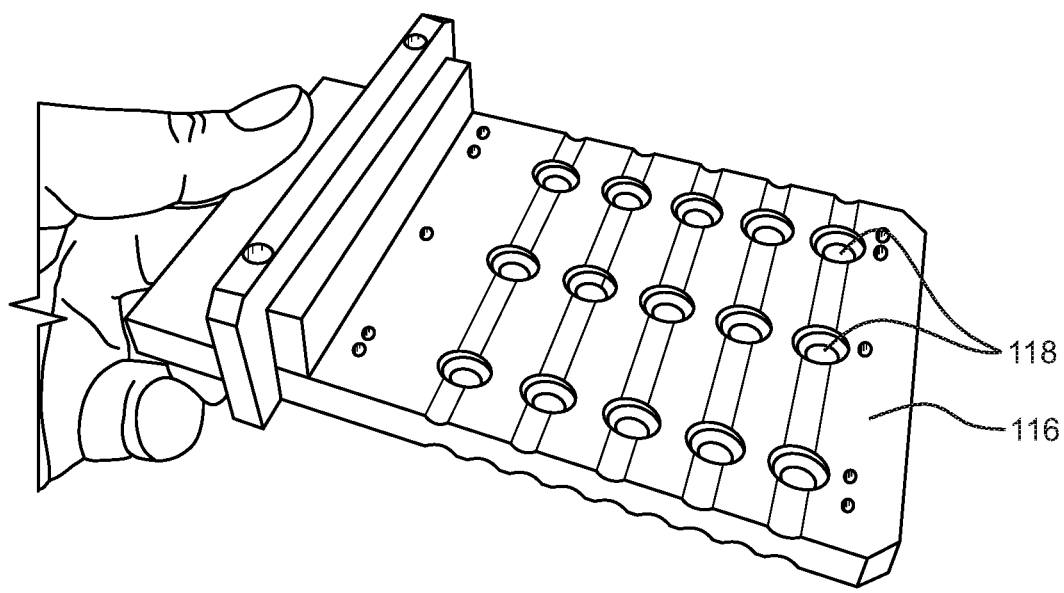
FIG. 3 is a diagrammatic perspective view of one non-limiting example of a tray element with pockets in accordance with the present disclosure.
Figure 4:
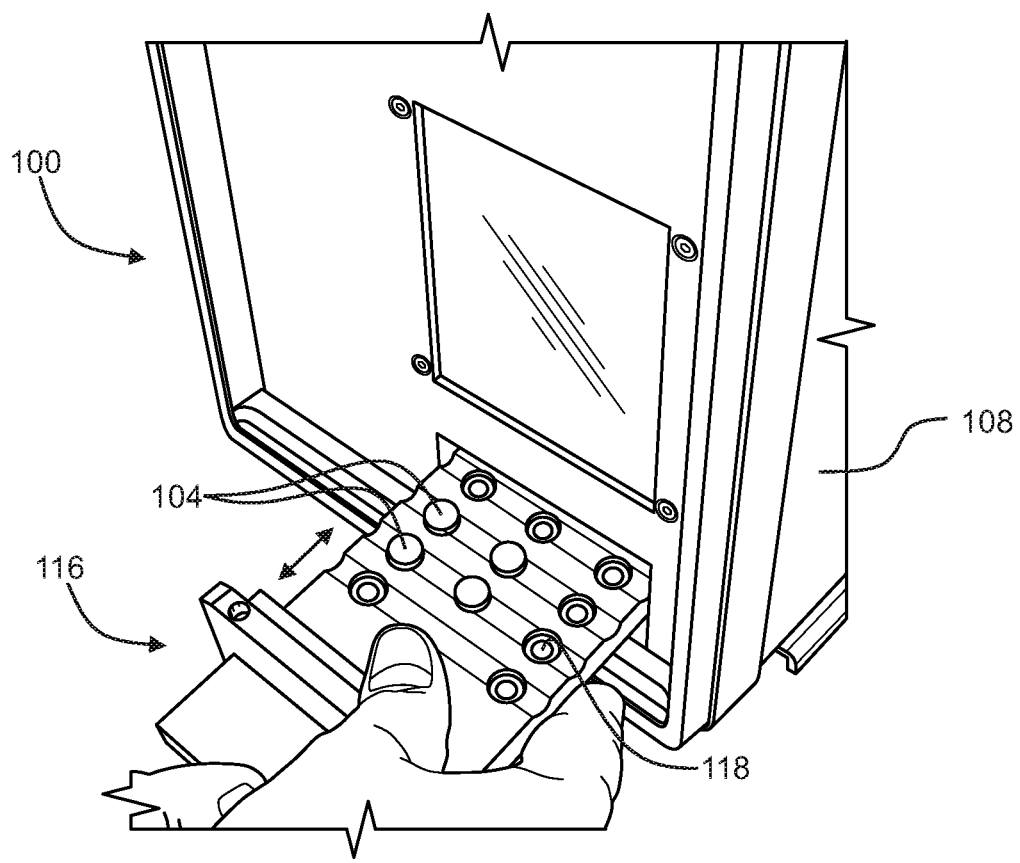
FIG. 4 is a diagrammatic perspective view of one non-limiting example of a tray element in accordance with the present disclosure being transported between a loading position and an application position.

Referring to FIG. 2 for example illustrations, the indelible identifiers 106 may be or include optically-viewable indelible images. In such case, each indelible image may include a facial image 172 of the respective patient 220 to whom the article was prescribed. Moreover, referring to FIG. 6, in such embodiment, the apparatus 100 may include or be configured to be placed in communication with a patient camera subsystem 174 for obtaining the facial image 172 at the point-of-sale location 102.

In particular embodiments of the apparatus, the indelible identifier 106 may include an RFID tag and the inspection element 114 may include an RFID reader.

In particular embodiments of the a portable, point-of-sale marking apparatus 100, (a) the discrete consumable articles 104 are defined as each comprising a precursor electrically-conductive layer prior to coming into contact with the apparatus 100; and (b) the application subsystem 112 includes a laser transmission element 122 configured to direct a steered beam of laser energy 124 toward the application zone 120 for (i) marking an indelible image 106 onto each said article within the application zone 120; and (ii) etching into the precursor electrically-conductive layer to form an RFID tag.

Referring to FIG. 15 for example illustration, in particular embodiments of the portable, point-of-sale marking apparatus 100, the tray element 116 may be or include an original equipment manufactured (OEM) pre-packaged blister back housing a plurality (e.g., an array) of said articles 104 in hermetically-sealed configuration, at least one side of the blister pack having a translucent or transparent layer 192 through which the indelible identifier application is achievable without compromising (e.g., breaking) the hermetic seal. In such an embodiment, the transport subsystem 110 may also include a shuttle element 126 slidable with respect to the enclosure 108 and configured to releasably support the tray element (e.g., as shown in FIG. 13).

Referring to FIG. 7, a system and method in accordance with the present disclosure may facilitate or comprise a series of steps. By way of a non-limiting example, a manufacturer 176 of pharmaceutical articles (e.g., opioid drugs) may supply the drug information (e.g., manufacturing date, lot, expiration date, shipping date, etc.) to the database element 150. The database element 150 may also receive information from any distribution point between the manufacturer 176 and the point-of-sale 102 (e.g., dispensing pharmacy or clinic). This step may operate, for example, similarly to a conventional courier tracking system. When the pharmacy 102 fills the prescription for a specific patient, that pharmacy may upload all the relevant data (e.g., prescribing physician 132 and patient names, addresses, drug quantity, etc.) into the same database element 150. The dispensing pharmacy 102 may then use the apparatus 100 to mark every solid dosage form (e.g., article 104) with a unique indelible identifier 106 linked to (associated with) the prescription. Referring to FIG. 2, such indelible identifier 106 may be, for example, a picture, a 2D code, an alphanumerical code, a cipher or any other combination of visible and/or invisible information (e.g., RFID). The dispensing pharmacy may then upload the identifier into the database element 150, thereby completing the cycle. The method may include an option for an automated subprocess whereby, for example, a prescribing physician enters a prescription into the database which randomly generates the UNIQUE ID, and the pharmacy then uses the apparatus 100 to mark this ID on every tablet/capsule while filling the prescription. Finally, the end user (e.g., patient) or other authorized personnel (e.g., nurse in the hospital, policemen on the street) can scan the tablet ID with an appropriate scanning device 156 (e.g., a cell phone) in network communication with the database element 150 and can determine what solid dosage form is under consideration and what it is intended for (e.g. date of manufacture, point of sale, physician and patient names, expiration date, etc.).

In one alternate embodiment of the method, the need for a database and scanning device may be eliminated and the dispensing pharmacy can just print, for example, a picture ID on each tablet. Other intermediate scenarios with incomplete or just local (e.g. hospital) databases are also possible. Notably, a database element 150 as described herein may comprise one or more processor elements, and one or more corresponding database components or memory storage devices, each of which may be located geographically remotely from one another.

Figure 20:
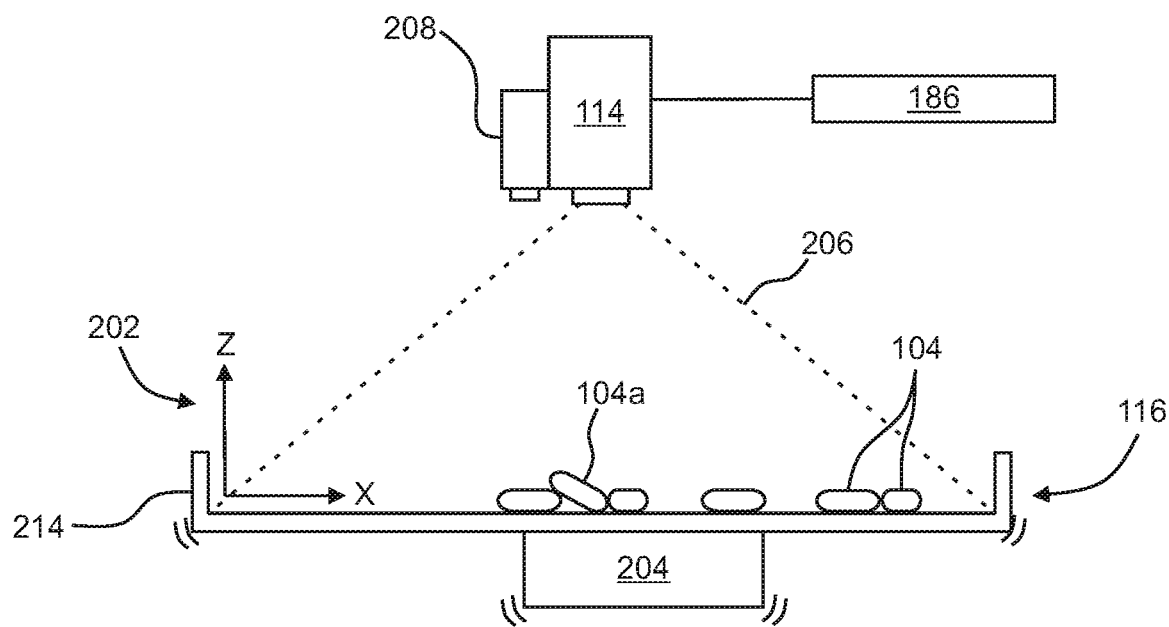
FIG. 20 is a diagrammatic cross-sectional view of portions of the example marking system of FIG. 19.

With reference to FIGS. 19 and 20, one or more of the portable point-of-sale marking apparatuses 100 in accordance with the present disclosure, or larger production-scale marking apparatuses with some or all of the same features and components as the portable version, may be configured to incorporate a randomized article marking system 200 in which a plurality of articles 104 can be randomly placed on the tray element 116 (e.g., by hand or by hopper mechanism) having a tray coordinate system 202, and then analyzed and marked by the system 200 in situ (i.e., without requiring the articles to be organized in an ordered array prior to marking). Once a plurality of articles 104 are placed on the tray element 116, an inspection camera 114 may obtain a first inspection image of the marking zone 120 within its field of view 206. The preliminary inspection image may then be analyzed (e.g., via one or more software modules) to determine various characteristics of the articles 104. By way of example, referring to FIG. 24, for each article 104 present within the marking field 120, the first inspection image (e.g., the image shown in FIG. 23) may be used assign a unique article identifier (e.g., alphanumeric) to each article 104 present within the marking zone 120, and to determine the respective article's X-Y position 210, angular orientation 212 (e.g., within the X-Y plane), shape, size, color and/or texture. These characteristics may then be stored as unique article datasets (e.g., in a dataset storage memory element), wherein each article dataset corresponds to a different article 104 within the marking zone 120 during the same inspection/marking cycle. The article dataset may then be used to produce a field marking image (e.g., by way of a respective marking image software module) to determine where and how the marking beam 124 should be activated and steered within the marking zone 120 in order to apply the proper markings (e.g., by way of laser transmission element 122, beam optics element 182, and beam scanning element 180) to each respective article 104. Finally, the inspection camera 114 may be configured to obtain a second inspection image to verify that each of the articles within the marking zone 120 were correctly marked and that the number of marked articles present within the applications/marking zone 120 (i.e., a batch) are counted. This article count may be recorded in a memory element configured to be in communication with or forming part of the control electronics 186. Additionally, or in the alternative, the article count may be recorded in a memory element configured to be in communication with or forming part of the remote database 150. Moreover, depending upon the particular embodiment of the apparatus 100, the inspection camera 114 may be configured or directed (i.e., by the control electronics 186) to obtain a count of the total number of articles 104 present within the application/marking zone 120, before, during and/or after the marking of all of the articles 104 present in the application/marking zone 120 has occurred. The apparatus 100 may be configured such that the article count corresponding to a particular batch of articles 104 may be printed onto a container in which the batch of marked articles will be placed for storage within the pharmacy or dispensing to the patient or the patient's care facility.

Figure 21:
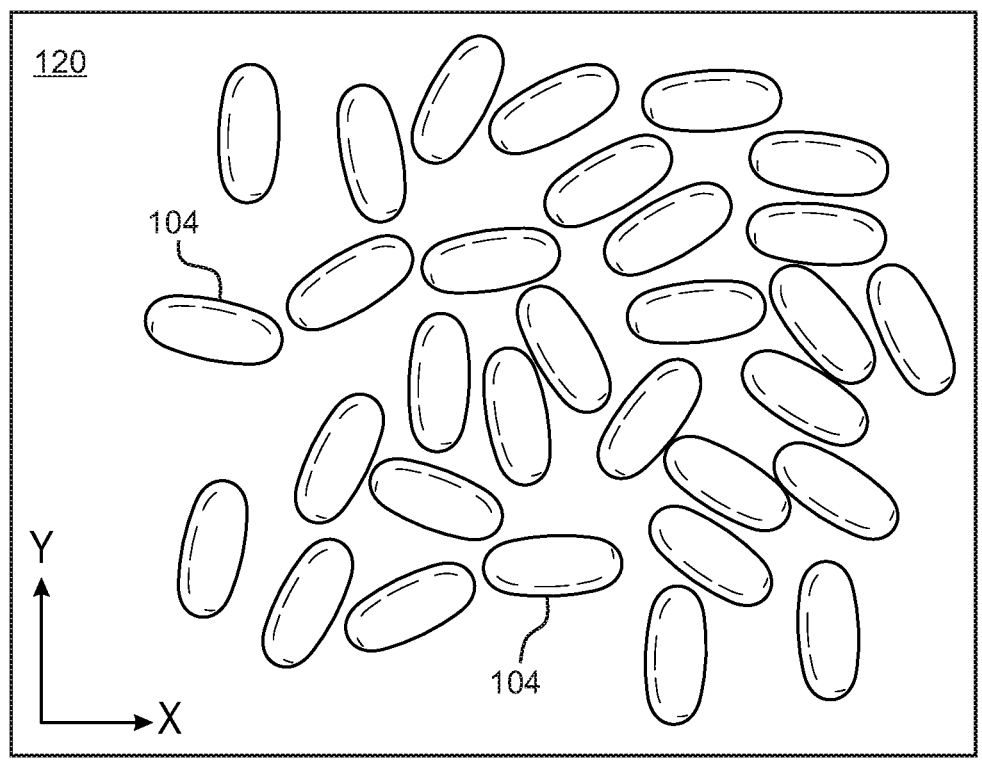
FIG. 21 is a diagrammatic top view of an inspection camera a field of view of a randomized article marking system in accordance with the present disclosure, such as the system of FIG. 19, wherein any overlapping articles in the application zone have been detected and then agitated to become non-overlapping.

Referring to FIGS. 19 and 20, embodiments of a randomized article marking system 200 may include one or more agitation elements 204 to ensure that none of the articles within the marking zone 120 overlap. Such agitation elements 204 may include, for example, a laterally-moving or circularly-moving blade or brush configured to sweep over the articles at a pre-determined height, or (as shown in FIG. 20) a vibration element 204 for momentarily vibrating the tray element 116. In particular embodiments of the system 200, these agitation elements may be employed as a matter of course regardless of whether an overlapping of the articles 104 has initially been detected. Alternatively, or in addition, embodiments of the system 200 may be configured to obtain a preliminary inspection image (e.g., preceding the first inspection image mentioned above) to determine any of the articles 104 in the marking zone 120 appear to be overlapping with another article 104 (see, e.g., overlapping/elevated article 104a). If it is determined that overlapping has or may have occurred, agitation element 204 may then be activated. A post-agitation image may also be obtained in order to verify that no instances of overlapping remain (see, e.g., FIG. 21) within the marking zone 120. A lateral boundary wall 214 may be provided to retain the articles on the tray 116 during, for example, agitation. The boundary wall be an integral part of the tray 116, or may be a separate component positioned in proximity to the periphery of the tray 116.

Figure 22:
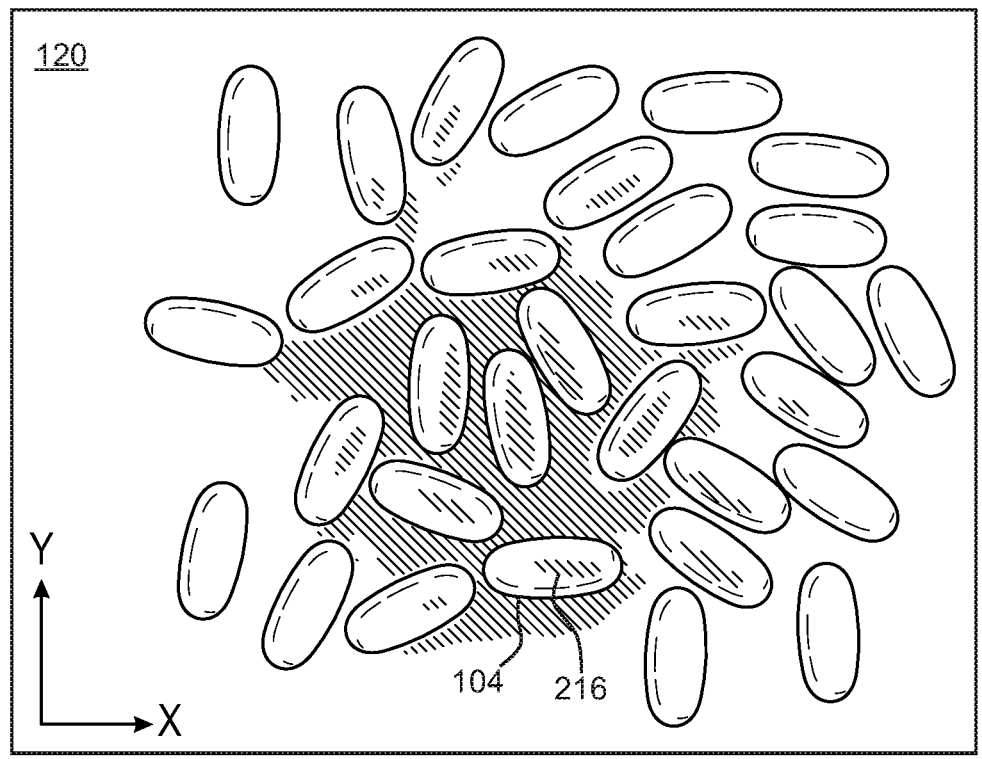
FIG. 22 is a diagrammatic top view of an inspection camera field of view similar to that of FIG. 21, but wherein the application zone is illuminated in such a way as to produce hotspots which may undesirably hinder accurate detection of the shapes of each of the articles within the application zone.
Figure 23:
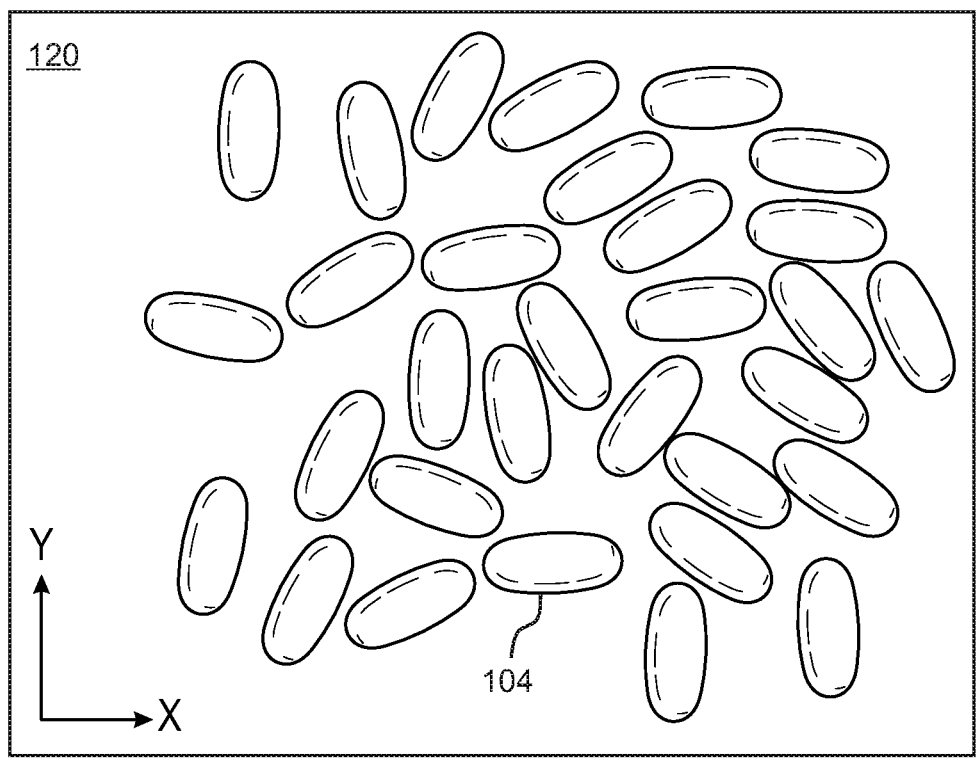
FIG. 23 is a diagrammatic top view of an inspection camera field of view similar to that of FIG. 22, but wherein the application zone is illuminated without hotspots (e.g., by way of diffused lights, filters, and/or software tools) in order to facilitate accurate identification of the shape of each article within the application zone.
Figure 24:
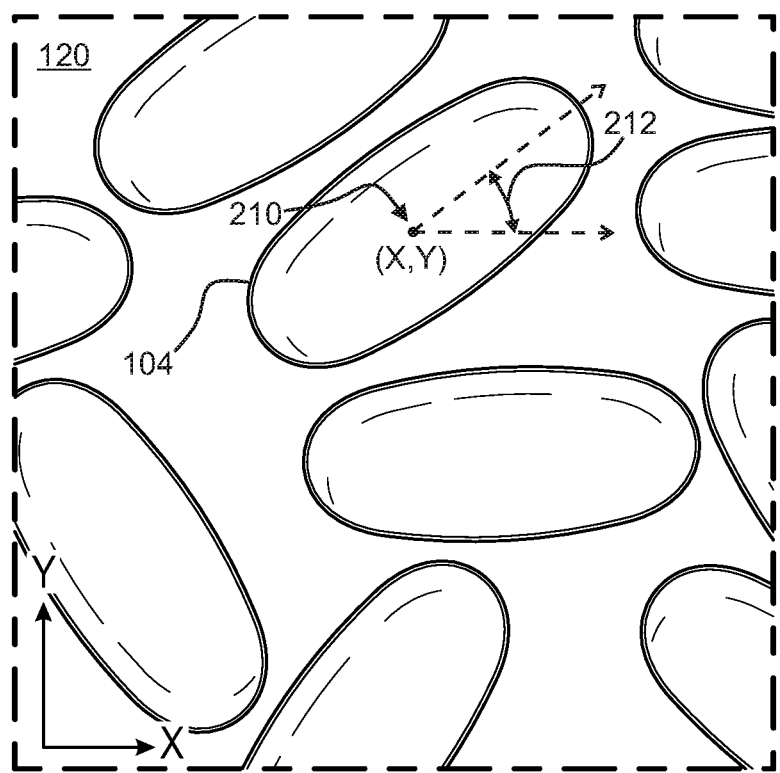
FIG. 24 is a diagrammatic top view of a portion of an inspection camera field of view similar to that of FIG. 22, but wherein a software process is used to find an origin and orientation of each article within the application zone.

Referring to FIG. 23, in certain embodiment of a randomized article marking system 200, the application/marking zone 120 may be illuminated by a field illumination element 208. In order to limit or prevent hotspots from being introduced in the image when the first inspection image is obtained (for example, the hotspot shown at 216 in FIG. 22), the illumination element 208 may include diffused lights, filters, and/or software tools, in order to facilitate accurate identification of the shape of each article 104 within the application zone. Referring to FIG. 24, a software process may be used to determine an X-Y origin 210 and orientation 212 of each article 104 within the application zone.

Notably, preferred embodiments of a randomized article marking system 200 may be configured to mark multiple different shapes and types of articles within the same marking or application zone 120 during the same inspection/marking cycle. By way of example, the system 200 may be capable of using the first inspection image to identify pharmaceutical tablets 104 of different types based on their shape, color and/or texture. This information may then be compared to a database (internal or external to the system 200) to allow the system 200 to identify the pharmaceutical composition of the respective tablets 104. This pharmaceutical composition information may then be used as a factor in controlling what indelible identifier 106 is marked into the respective article 104.

Figure 25:
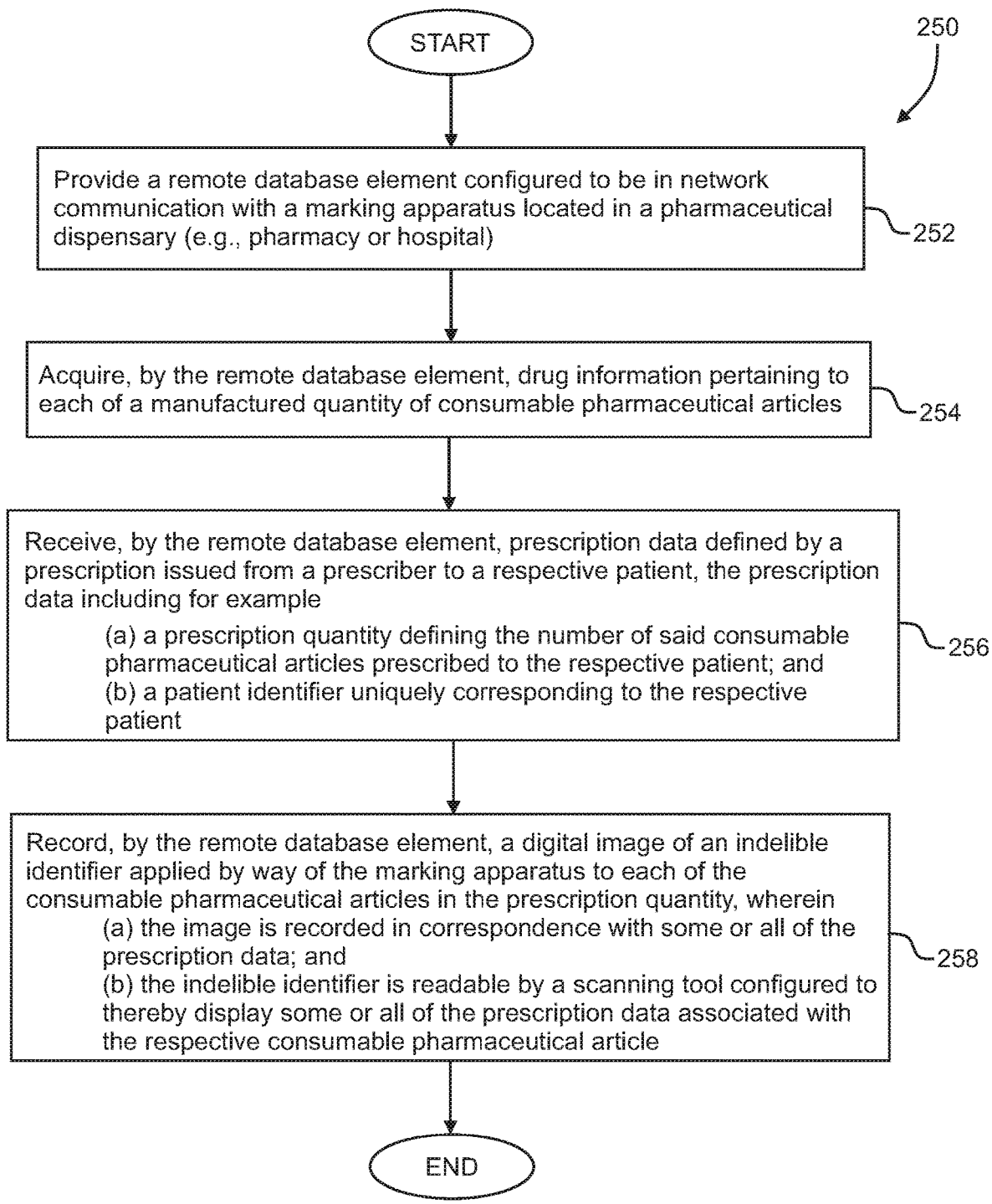
FIG. 25 is a diagrammatic flow chart of one example implementation of a method for facilitating tracking of consumable pharmaceutical articles in accordance with the present disclosure.

Referring to FIGS. 7 and 25, particular preferred embodiments of a method 250 for facilitating tracking of consumable pharmaceutical articles 104 are disclosed herein. For example, at block 252, a remote database element 150 may be provided which is configured to be in network communication with a marking apparatus 100 located in a pharmaceutical dispensary 102. The pharmaceutical dispensary 102 may be a point-of-sale location at which the patient is dispensed the prescribed quantity of articles 104 (e.g., a pharmacy or hospital).

At block 254, a remote database element 150 may acquire drug information pertaining to each of a manufactured quantity of consumable pharmaceutical articles. At block 256, the remote database element 150 may receive prescription data defined by a prescription issued from a prescriber 132 to a respective patient. This prescription data may include, for example, (a) a prescription quantity defining the number of said consumable pharmaceutical articles prescribed to the respective patient; and (b) a patient identifier (e.g., the patient's name) uniquely corresponding to the respective patient. In certain embodiments of the method, the step of receiving may be by way of network communication between the prescriber 132 and the remote database element 150. The prescription quantity of articles would typically comprise a subset of the manufactured quantity of articles.

At block 258, the remote database element 150 may record a digital image of an indelible identifier 106 applied by way of the marking apparatus 100 to each of the consumable pharmaceutical articles 104 in the prescription quantity. The digital image may preferably be recorded in correspondence with some or all of the prescription data. In certain embodiments of the method, the digital image may be generated by the marking apparatus 100 and obtained by the remote database element 150 prior to the step of recording. Notably, the digital image may be, for example, a graphical reproduction of the indelible identifier (e.g., as raster or vector image data) or some other optically-readable or signal-readable data format that informationally mirrors the indelible identifier.

The indelible identifier 106 may be configured to be readable by a scanning tool 156 configured to thereby display some or all of the prescription data associated with the respective consumable pharmaceutical article 104. The indelible identifier 106 may preferably be an alpha-numeric code, photo image (e.g., the face of the patient), a bar code, a QR code, a cipher, an RFID code some combination thereof or the like. The indelible identifier 106 is preferably uniquely associated with the respective prescription.

The drug information may include one or more of the following: manufacturing date, a lot number, an expiration date and a shipping date. The drug information may be acquired from a distributor or manufacturer 176 of the manufactured quantity by way of network communication with the remote server element 150.

The prescription data may further include one or more of the following: name of the prescriber 132, name of the patient 220, address of the patient, location of the pharmaceutical dispensary, prescription number, article dosage (e.g., strength) and article expiration date.

In particular preferred embodiments of the method, prior to the step of recording, the remote database element 150 may generate the digital image. The remote database element 150 may then provide the digital image to the marking apparatus 100 for application of the indelible identifier onto or within the articles 104.

In certain preferred embodiments of the method, the remote database element 150 may be configured to be placed in network communication with the scanning tool 156 to thereby provide the prescription data to the scanning tool for the display of the prescription data.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A portable, point-of-sale marking apparatus for applying indelible identifiers onto discreet consumable pharmaceutical articles, the apparatus comprising:
   an enclosure;
   a transport subsystem configured to transport a tray element between a loading position and an application position, the tray element having a multiplicity of pockets each configured to retain a respective said article, wherein
      (a) when the tray element is in the application position, its pockets are located within an application zone internal to the enclosure, and
      (b) when the tray element is in the loading position, its pockets are located externally to the enclosure;
   an identifier application subsystem positioned within the enclosure for applying an indelible identifier onto each said article within the application zone; and
   an inspection element positioned within the enclosure and configured to verify the quality of the indelible identifier applied onto each respective article.

2. A portable, point-of-sale marking apparatus as defined in claim 1, wherein the identifier application subsystem includes a laser transmission element configured to direct a steered beam of UV laser energy toward the application zone for marking an indelible image onto each said article within the application zone.

3. A portable, point-of-sale marking apparatus as defined in claim 1, wherein the enclosure is unitary.

4. A portable, point-of-sale marking apparatus as defined in claim 1, wherein the transport subsystem includes a shuttle element slidable with respect to the enclosure and configured to releasably support the tray element.

5. A portable, point-of-sale marking apparatus as defined in claim 4, wherein the apparatus includes a tray identification reader, and the tray element includes a tray identification element readable by the tray identification reader.

6. A portable, point-of-sale marking apparatus as defined in claim 5, wherein the apparatus includes a plurality of tray elements, the pockets of each of said plurality of tray elements having a different size compared to the pockets of the other tray elements.

7. A portable, point-of-sale marking apparatus as defined in claim 1, wherein the enclosure includes an application zone window portion disposed between the application position and the loading position, the application zone window portion being configured to enable a naked eye of a human to view the occurrence of the application from a viewpoint outward of the enclosure without causing damage to the eye.

8. A portable, point-of-sale marking apparatus as defined in claim 1 further comprising a network communication element configured to be placed in network communication with a remote database.

9. A portable, point-of-sale marking apparatus as defined in claim 1, wherein the indelible identifier includes article identifier data unique to the article upon which it is applied.

10. A portable, point-of-sale marking apparatus as defined in claim 9, wherein the article identifier data includes patient data for identifying a patient to whom the respective article was prescribed and sold.

11. A portable, point-of-sale marking apparatus as defined in claim 9, wherein the article identifier data includes prescriber data for identifying a prescriber by whom the respective article was prescribed.

12. A portable, point-of-sale marking apparatus as defined in claim 9, wherein the article identifier data includes prescription data for identifying the prescription number under which the respective article was sold.

13. A portable, point-of-sale marking apparatus as defined in claim 8, wherein the remote database is in data-receiving communications with a pharmaceutical manufacturer or distributor.

14. A portable, point-of-sale marking apparatus as defined in claim 8, wherein the remote database is in network communication with a law enforcement scanning tool, the scanning tool being configured to read the indelible identifier and indicate whether the indelible identifier corresponds to the patient to whom the respective article was prescribed and sold.

15. A portable, point-of-sale marking apparatus as defined in claim 1 further comprising a layer-depositing element for depositing one or more layers of digestible material onto the articles, the one or more layers being configured to indicate whether and when the articles have been consumed by a patient.

16. A portable, point-of-sale marking apparatus as defined in claim 1 wherein the identifier application subsystem includes a sleeve-encapsulation element for encapsulating each of the articles with a respective sensor sleeve, the sensor sleeves each having a sensor imbedded therein.

17. A portable, point-of-sale marking apparatus as defined in claim 1 wherein said identifier application subsystem includes a marking layer applicator by which the indelible identifier is applied onto each said article within the application zone.

18. A portable, point-of-sale marking apparatus as defined in claim 17 wherein the marking layer applicator is configured to deposit one or more layers of a marking substrate composition onto each said article within the marking zone, the marking substrate composition comprising Titanium Dioxide.

19. A portable, point-of-sale marking apparatus as defined in claim 18 wherein the deposition is by way of a spraying operation.

20. A portable, point-of-sale marking apparatus as defined in claim 18 wherein the identifier application subsystem includes a laser transmission element configured to direct a steered beam of UV laser energy toward the application zone for marking an indelible image onto the marking substrate composition deposited onto each said article within the application zone.

21. A portable, point-of-sale marking apparatus as defined in claim 1 wherein the inspection element is an inspection camera.

22. A portable, point-of-sale marking apparatus as defined in claim 1 wherein the indelible identifiers are or include optically-viewable indelible images.

23. A portable, point-of-sale marking apparatus as defined in claim 22 wherein each indelible image includes a facial image of the respective patient to whom the article was prescribed.

24. A portable, point-of-sale marking apparatus as defined in claim 23 wherein the apparatus is configured to be placed in communication with a patient camera subsystem for obtaining the facial image.

25. A portable, point-of-sale marking apparatus as defined in claim 1 wherein the indelible identifier includes an RFID tag and the inspection element includes an RFID reader.

26. A portable, point-of-sale marking apparatus as defined in claim 1 wherein
  (a) the discrete consumable articles are defined as each comprising a precursor electrically-conductive layer prior to coming into contact with the apparatus; and
  (b) the identifier application subsystem includes a laser transmission element configured to direct a steered beam of laser energy toward the application zone for
    (i) marking an indelible image onto each said article within the application zone; and
    (ii) etching into the precursor electrically-conductive layer to form an RFID tag.

27. A portable, point-of-sale marking apparatus as defined in claim 1, wherein the tray element is a pre-packaged blister back housing a plurality of said articles in hermetically-sealed configuration, at least one side of the blister pack having a translucent or transparent layer through which the indelible identifier application is achievable without compromising the hermetic seal.

* * * * *